United States Patent
Koob et al.

(10) Patent No.: US 12,070,528 B2
(45) Date of Patent: *Aug. 27, 2024

(54) COLLAGEN AND MICRONIZED PLACENTAL TISSUE COMPOSITIONS AND METHODS OF MAKING AND USING THE SAME

(71) Applicant: MiMedx Group, Inc., Marietta, GA (US)

(72) Inventors: Thomas J. Koob, Marietta, GA (US); Michelle Massee, Marietta, GA (US)

(73) Assignee: MiMedx Group, Inc., Marietta, GA (US)

( * ) Notice: Subject to any disclaimer, the term of this patent is extended or adjusted under 35 U.S.C. 154(b) by 896 days.

This patent is subject to a terminal disclaimer.

(21) Appl. No.: 16/989,170

(22) Filed: Aug. 10, 2020

(65) Prior Publication Data

US 2021/0015972 A1    Jan. 21, 2021

Related U.S. Application Data

(63) Continuation of application No. 15/040,936, filed on Feb. 10, 2016, now Pat. No. 10,736,990.

(Continued)

(51) Int. Cl.
| | |
|---|---|
| *A61L 27/36* | (2006.01) |
| *A61K 9/14* | (2006.01) |
| *A61K 9/70* | (2006.01) |
| *A61K 35/50* | (2015.01) |
| *A61K 38/39* | (2006.01) |
| *A61L 26/00* | (2006.01) |

(Continued)

(52) U.S. Cl.
CPC ............ *A61L 27/3604* (2013.01); *A61K 9/14* (2013.01); *A61K 9/7007* (2013.01); *A61K 35/50* (2013.01); *A61K 38/39* (2013.01); *A61L 26/0033* (2013.01); *A61L 26/0057* (2013.01); *A61L 26/0061* (2013.01); *A61L 26/0095* (2013.01); *A61L 27/24* (2013.01); *A61L 27/54* (2013.01); *A61L 2430/10* (2013.01); *A61L 2430/34* (2013.01)

(58) Field of Classification Search
None
See application file for complete search history.

(56) References Cited

U.S. PATENT DOCUMENTS

| | | |
|---|---|---|
| 8,067,044 B2 | 11/2011 | Henry et al. |
| 8,323,701 B2 | 12/2012 | Daniel et al. |

(Continued)

FOREIGN PATENT DOCUMENTS

| | | |
|---|---|---|
| JP | 2014-505111 A | 2/2014 |
| JP | 2014-138590 A | 7/2014 |

(Continued)

OTHER PUBLICATIONS

International Search Report & Written Opinion for PCT Application No. PCT/IB2016/050713, May 23, 2016.

(Continued)

*Primary Examiner* — Thomas J. Visone
(74) *Attorney, Agent, or Firm* — Alston & Bird LLP

(57) ABSTRACT

Described herein are compositions of collagen and micronized placental tissue components, methods for producing the same and methods for using the same for wound healing, repairing damaged tendons, cosmetic applications and covering biocompatible materials and/or devices.

18 Claims, 5 Drawing Sheets

Related U.S. Application Data

(60) Provisional application No. 62/115,109, filed on Feb. 11, 2015.

(51) Int. Cl.
*A61L 27/24* (2006.01)
*A61L 27/54* (2006.01)

(56) References Cited

U.S. PATENT DOCUMENTS

| | | |
|---|---|---|
| 8,357,403 B2 | 1/2013 | Daniel et al. |
| 8,372,437 B2 | 2/2013 | Daniel |
| 8,409,626 B2 | 4/2013 | Daniel et al. |
| 8,623,421 B2 | 1/2014 | Daniel |
| 8,709,494 B2 | 4/2014 | Daniel |
| 9,186,382 B2 | 11/2015 | Daniel et al. |
| 9,655,948 B1 | 5/2017 | Koob et al. |
| 9,827,293 B2 | 11/2017 | Koob et al. |
| 9,943,551 B2 | 4/2018 | Koob et al. |
| 10,105,398 B2 | 10/2018 | Morse et al. |
| 2002/0082697 A1 | 6/2002 | Damien |
| 2007/0071828 A1 | 3/2007 | Tseng et al. |
| 2008/0118947 A1 | 5/2008 | Yu et al. |
| 2013/0202676 A1 | 8/2013 | Koob et al. |
| 2013/0344162 A1 | 12/2013 | Morse et al. |
| 2014/0050788 A1 | 2/2014 | Daniel et al. |
| 2014/0052247 A1 | 2/2014 | Daniel et al. |
| 2014/0067058 A1 | 3/2014 | Koob et al. |
| 2014/0106447 A1 | 4/2014 | Brown et al. |
| 2014/0205646 A1 | 7/2014 | Morse et al. |
| 2014/0302162 A1 | 10/2014 | Morse et al. |
| 2014/0343688 A1 | 11/2014 | Morse et al. |
| 2015/0017255 A1 | 1/2015 | Koob et al. |
| 2015/0064274 A1 | 3/2015 | Koob |
| 2015/0086634 A1 | 3/2015 | Koob et al. |
| 2016/0067287 A1 | 3/2016 | McQueen et al. |

FOREIGN PATENT DOCUMENTS

| | | |
|---|---|---|
| WO | WO-2012/112410 A2 | 8/2012 |
| WO | WO-2014/113733 A1 | 7/2014 |

OTHER PUBLICATIONS

Office Action for European Application No. 16711018.8 dated Feb. 6, 2019, 5 pages.

Office Action for Japanese Application No. 2017-541673 dated Oct. 21, 2019, 6 pages including English translation.

Office Action for Japanese Application No. 2021-028785 dated Mar. 29, 2022, 6 pages including English translation.

U.S. Appl. No. 15/040,936, filed Feb. 10, 2016, U.S. Pat. No. 10,736,990, Issued.

Placental Collagen

Placental Collagen with Micronized Placental

Placental Collagen

Placental Collagen with Micronized Placental

COLLAGEN AND MICRONIZED PLACENTAL TISSUE COMPOSITIONS AND METHODS OF MAKING AND USING THE SAME

CROSS REFERENCE TO RELATED APPLICATIONS

This application is a continuation of U.S. application Ser. No. 15/040,936, filed Feb. 10, 2016, which claims the benefit of U.S. Provisional App. No. 62/115,109, filed Feb. 11, 2015, which are incorporated herein by reference in their entirety.

FIELD OF THE INVENTION

This invention relates to compositions composed of water, collagen and micronized placental tissue components and methods for making the same. In certain aspects, the compositions of this invention are useful in applications such as wound healing, repairing damaged tendons, cosmetic applications and covering biocompatible materials and/or devices.

BACKGROUND

Human placental membrane (e.g. amniotic membrane) has been used for various types of reconstructive surgical procedures since the early 1900s. The membrane serves as a substrate material, more commonly referred to as a biological dressing or tissue graft. Such a membrane has also been used for ophthalmic procedures and more recently for dental regenerative procedures, treating ulcers, and as an adhesion barrier. Typically, the membrane is either frozen or dried for preservation and storage.

Placental tissue is typically harvested after an elective Cesarean surgery. The placenta is composed of the amniotic sac and sometimes is meant to include the umbilical cord and amniotic sac. The amniotic sac contains the amniotic fluid and protects the fetal environment.

The amniotic sac, commonly referred to as the amniotic membrane, has two primary layers of tissue, amnion and chorion which are separated by a thin connective layer which is sometimes referred to as the intermediate layer. Amnion is the innermost layer of the amniotic sac and is in direct contact with the amniotic fluid. Histological evaluation indicates that the membrane layers of the amnion consist of a single layer of epithelium cells, thin reticular fibers (basement membrane), a thick compact layer, and a fibroblast layer. The fibrous layer of amnion (i.e., the basement membrane) contains collagen types IV, V, and VII, and cell-adhesion bio-active factors including fibronectin and laminins.

Placental tissue, such as amnion membrane, provides unique characteristics when used for surgical and wound-healing procedures, including providing a matrix for cellular migration/proliferation, providing a natural biological barrier, is non-immunogenic, and contains numerous bio-active molecules. Placental tissue can be used as a membrane to assist in tissue regeneration and improved healing outcomes in numerous applications. The amnion has the capability to self-adhere or, in the alternative, is susceptible of being fixed in place using different techniques, including fibrin glue or suturing.

Placental tissue grafts have been used in a variety of medical applications, including wound care and cosmetics. However, these tissue grafts lack flexibility and/or coherency especially in environments where shear is common. Accordingly, there is a need to provide placental tissue compositions with enhanced flexibility and/or coherency.

Micronized placental tissue components have been previously disclosed and used in an aqueous suspension for injection into injured body components such as tendons, ligaments, etc. However, notwithstanding the beneficial properties imparted in healing such injuries, it would be desirable to provide for a composition which retains its position once injected into the body.

SUMMARY OF THE INVENTION

This invention is predicated, at least in part, on the discovery that an aqueous suspension of micronized placental tissue components and collagen provides for a solid mass with unexpected properties including enhanced flexibility and/or cohesion. It was further surprising that such properties could be enhanced upon application of suitable shear and force, such as upon ejection from a syringe. The ability to target a desired level of consistency and cohesiveness of the composition by altering the ratios of the primary components (water, collagen, and micronized placental tissue) was also unexpected. The resulting solid mass compositions are especially suited for wound healing, tendon repair, cosmetic applications and covering biocompatible materials and/or devices.

Without being bound by theory, it is believed that the combination of aqueous collagen with micronized placental tissue provides a more effective composition for tissue regeneration and/or stem cell recruitment than either component alone. For example, the collagen provides a scaffold and/or filler to the region where the composition is applied, and the micronized placental tissue provides biological activity (growth factors, stem cell recruitment, and the like). Further, the compositions as described herein are particularly suited for cosmetic applications.

In one aspect of this invention is provided a composition of water, collagen and micronized placental tissue components such that the composition is an integrated admixture having apparent homogeneity. In other aspects, a collagen and micronized placental tissue component composition is provided having apparent homogeneity as well being a coherent and flexible mass.

In one aspect of this invention is provided a method for transforming an aqueous/gelatinous collagen mass into a coherent and flexible composition. The method comprising incorporating sufficient micronized placental tissue into the aqueous collagen material and applying sufficient force and shear to the composition so as to transform the composition into a coherent, flexible mass.

The compositions of this invention can be used for assisting in the healing of wounds such as damaged tendons. The compositions of this invention can also be used for cosmetic applications or to cover biocompatible materials and/or devices.

In one embodiment, the micronized placental tissue components comprise micronized amnion, chorion, Wharton's jelly, or any combination thereof. In one embodiment, the micronized components have a particle size less than 400 µm.

In one embodiment, the micronized placental tissue components are obtained by micronizing a tissue graft comprising an amnion layer and a chorion layer, wherein the chorion layer is layered directly over the amnion layer, and further wherein the amnion layer has an exposed basement membrane and an intact fibroblast component. In another embodiment, the micronized placental tissue comprises an amnion layer and a chorion layer, wherein the chorion layer is layered directly over the amnion layer, and further wherein the amnion layer has an intact epithelial cell layer and an intact fibroblast component.

In one embodiment, the collagen is human collagen, for example, human placental collagen. In one embodiment, the collagen is an aqueous collagen material comprising from about 0.1% to about 2% collagen.

In one embodiment, the weight ratio of micronized placental tissue to collagen is from about 3:1 to about 100:1. In another embodiment, the weight ratio of micronized placental tissue components to collagen is about 100:1 to about 300:1. In a preferred embodiment, the weight ratio of micronized placental tissue to collagen is about 50:1.

In one embodiment, the composition is coherent and flexible under physiological conditions, for example, a temperature range of about 15° C. to about 45° C.

In another embodiment, the composition is obtained by ejecting a precursor composition comprising an aqueous/gelatinous collagen and micronized placental tissue components. In yet other embodiments, the precursor composition comprising an aqueous/gelantinous mass is in the form of a gel, putty or paste.

The advantages of the invention will be set forth in part in the description which follows, and in part will be apparent from the description, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The accompanying drawings, which are incorporated in and constitute a part of this specification, illustrate several aspects described below.

DETAILED DESCRIPTION

Figure 1:
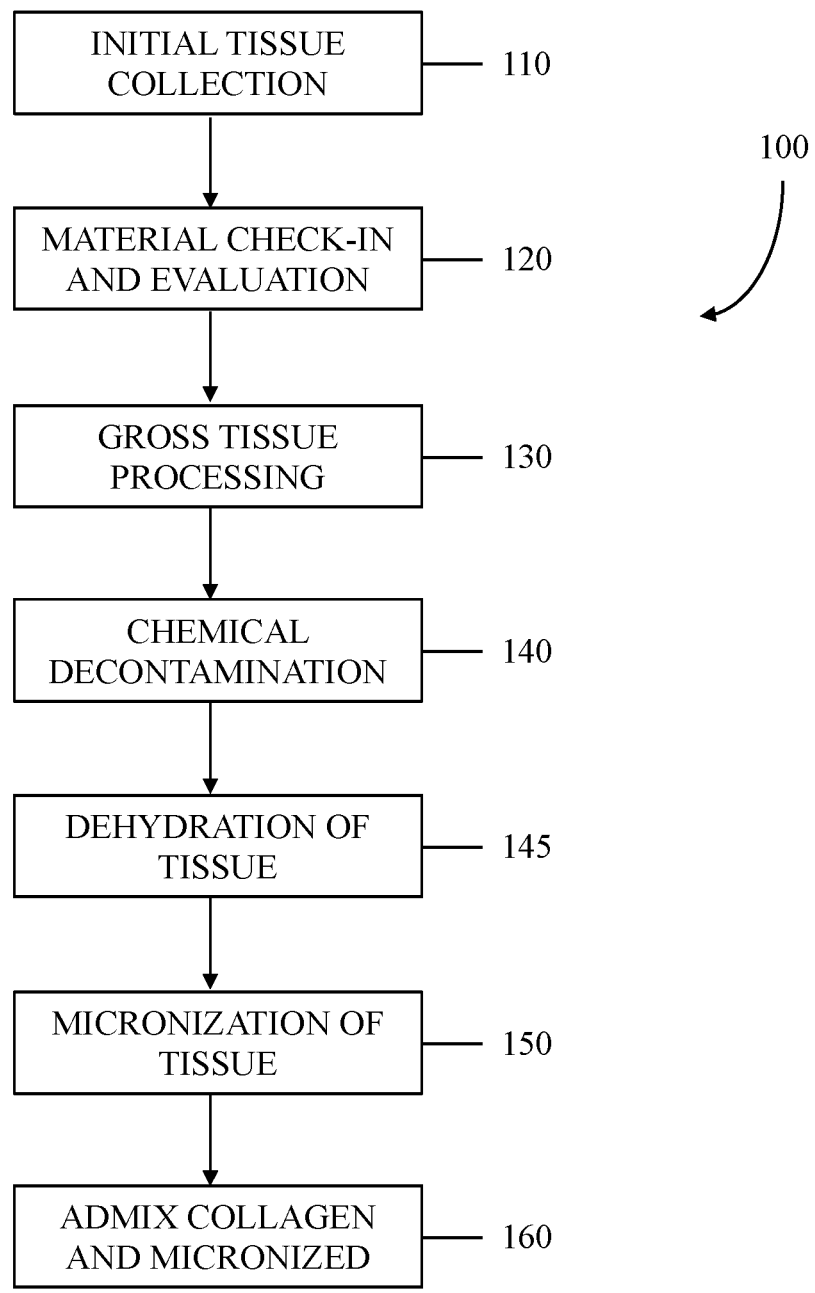
FIG. 1 is an overview flow chart of the process for making the coherent, flexible hydrated collagen compositions described herein.

Before the present invention is disclosed and described, it is to be understood that the aspects described below are not limited to specific compositions, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

It must be noted that, as used in the specification and the appended claims, the singular forms "a," "an" and "the" include plural referents unless the context clearly dictates otherwise. Thus, for example, reference to "a cross-linking agent" includes mixtures of two or more such agents, and the like.

"Optional" or "optionally" means that the subsequently described event or circumstance can or cannot occur, and that the description includes instances where the event or circumstance occurs and instances where it does not. For example, the phrase "optionally cleaning step" means that the cleaning step may or may not be performed.

The term "subject" as used herein is any vertebrate organism including mammals such as domesticated animals and primates such humans. In a preferred embodiment, the subject is a human.

The term "about" as used herein indicates that a value can vary by up to ±5%, for example ±5%, ±2%, or ±1%.

The terms "coherent," "coherency," and "cohesion" are used herein to refer to a composition that retains its homogenous mass after formation at a temperature from at least 0° C. to about 40° C. That is to say that the mass once formed, does not separate into individual components or disintegrate into smaller particles when maintained ex vivo at a temperature from at least 0° C. to about 40° C. Stated another way, the composition is sufficiently coherent such that it does not break, splinter, disintegrate or fragment prior to and during introduction into or onto a subject. The suitable coherency can be determined by one skilled in the art based on the purpose for the introduction, the amount of placental tissue composition to be used, the manner of administration/introduction, and the specific body part for administration.

While the compositions are coherent upon administration, it is understood that endogenous enzymes such as collagenases, proteases, etc. will erode these compositions. During erosion, growth factors and other biological factors are released over time from the micronized placental tissue thereby providing for sustained release of such factors at the location of administration/introduction.

The term "flexible" and "flexibility" are used interchangeably herein to refer to the ability of a material to shape change when a force is applied. A material that is more flexible than another is more able to shape change. The degree of flexibility of the composition will vary depending on the application, the amount of placental tissue components used, and the like. For the uses that require reduced flexibility, that flexibility is decreased by increasing the amount of placental tissue components, for example compositions that contain a micronized placental tissue component to collagen weight ratio of at least 100:1. For those compositions that require less flexibility, the weight ratio of micronized placental tissue components to collagen is increased to approximately 300:1. One of skill in the art would be able to determine the optimal flexibility of the composition appropriate for the specific application. The flexibility of the collagen and micronized placental tissue compositions can be modified by altering the ratios of collagen and micronized placental tissue.

For those uses that require increased flexibility, the flexibility is increased by decreasing the amount of micronized placental tissue components, for example coherent compositions that contain a micronized placental tissue components to collagen weight ratio of less than 100:1. The greater the amount of micronized placental tissue the less flexible the composition.

Compositions having a weight ratio of micronized placental tissue components to collagen from about 1:1 to about less than 100:1 maintain a gel-like composition wherein the gel-like composition has apparent homogeneity of the micronized placental tissue components throughout the mass. As is apparent, each of embodiments has uses for particular environments. For example, a gelatinous mass of apparent homogeneity may be readily injected into a joint; a coherent, flexible mass may be used for cosmetic purposes, such as wrinkles; and a coherent, less flexible mass may be used as a wound care covering for burns.

The term "apparent homogeneity" as used herein refers to a composition of collagen and micronized placental tissue components which shows no substantial distinction between the collagen and placental tissue components and wherein the placental tissue components are uniformly dispersed throughout. For example, there may be no substantial distinction between the collagen and placental tissue components when visualized without magnification. In other compositions, there may be no substantial distinction between the collagen and placental tissue components when visualized under magnification. Apparent homogeneity of the collagen and micronized placental tissue components may be created through force and/or shear applied to the composition. For example, force and/or shear can be applied by pressure in a mold or press, ejection through a syringe, or other methods common in the field. Apparent homogeneity of the collagen micronized placental tissue components may be achieved by mixing the composition until there is no substantial distinction between the collagen and placental tissue components and wherein the placental tissue components are uniformly dispersed throughout.

The term "amnion" as used herein includes isolated amniotic membrane where the intermediate tissue layer has been substantially removed. The amnion preferably is obtained from the placenta. In some embodiments, the amnion is obtained from the umbilical cord.

The term "placental tissue" refers to any and all of the well-known components of the placenta including but not limited to amnion, chorion, and when referring to umbilical cord as part of the placenta—Wharton's jelly, and the like (but not the entire placenta). In one preferred embodiment, the placental tissue does not include any of the umbilical cord components (e.g., Wharton's jelly, umbilical cord vein and artery, and surrounding membrane). In a preferred embodiment, the placental tissue is modified typically by removing the intermediate layer between the amnion and chorion such that the resulting composition lacks this layer.

In view of the above, the processing of placental tissue requires that steps be taken to prevent cross-contamination from one processed placental tissue to the next. Such steps involve the assembly of sterile supplies and equipment in a staging area that is in a controlled, aseptic environment, and the placental tissue is prepared for introduction into the aseptic controlled environment as described herein. If the controlled environment is a manufacturing hood, the sterile supplies are opened and placed into the hood using conventional aseptic technique. If the controlled environment is a clean room or similar aseptic room, the sterile supplies are opened and placed on a cart covered by a sterile drape. All work surfaces are covered by a piece of sterile drape using conventional aseptic techniques, and the sterile supplies and the processing equipment are placed on to the sterile drape, again using conventional aseptic techniques. In addition, any processing equipment that is utilized with a first placental tissue must be decontaminated according to conventional and industry-approved decontamination procedures prior to the use of the equipment for processing a subsequent non-autologous placental tissue (i.e., from a different donor), which requires removing, decontaminating, and then re-introducing the equipment into the controlled environment.

The term "placental tissue graft" refers to any combination of placental tissue which contains either an amnion or a chorion layer and optionally additional layers which may or may not be obtained from the placenta. Preferably, the placental tissue graft lacks an intermediate layer. Single layers of amnion or chorion can be used. However, preferably multiple layers of amnion and/or chorion form the tissue graft, which layers are typically dehydrated and laminated together. The amnion can optionally be partially or completely decellularized such as by removing substantially all of the epithelial layer and/or the fibroblast layer. Examples of placental tissue grafts suitable for this invention include, by way of example only, those described in U.S. Pat. Nos. 8,323,701; 8,372,437; and U.S. Patent Publication Nos. 2014/0052247; 2014/0067058; 2014/0205646; and 2013/0202676, each of which is incorporated herein by reference in its entirety.

As used herein, the term "tensile strength" refers to the resistance of a composition to longitudinal stress, as measured by the minimum amount of longitudinal stress required to rupture the material. Tensile strength can be determined by any method known in the art. For example, Young's modulus, also known as tensile modulus, is a measure of the stiffness of a material. It is defined as the ratio of the uniaxial stress over the uniaxial strain in the range of stress in which Hooke's Law holds. A uniaxial electromechanical materials testing system, such as an Instron Model 5565 or Instron Tester Model 1122, may be employed to determine tensile strength.

As used herein, the term "non-autologous tissue" refers to placental tissue from a different placenta donor.

Titles or subtitles may be used in the specification for the convenience of a reader, which are not intended to influence the scope of the present invention. Additionally, some terms used in this specification are more specifically defined below.

Collagen and Micronized Placental Tissue Compositions and Methods for Making Thereof Described herein are coherent, flexible compositions composed of hydrated collagen and micronized placental tissue components. In one aspect, the composition includes water, collagen and micronized placental tissue components. Preferred compositions can be prepared, for example, by the route described below. Such compositions are prepared from micronized placental tissue components, which are described, for example, in PCT Application Pub. No. WO 2012112410, as well as in U.S. Patent Application Pub. Nos.

2013/0344162; and 2014/0050788. The contents of these applications are specifically incorporated by reference in their entireties.

It is understood that the term "micronized" is meant to include micron and sub-micron sized placental tissue particles.

A brief overview of certain aspects of the steps to harvest, process, and prepare placental material for later use as a collagen and micronized placental tissue composition are described below and depicted in FIG. 1. More detailed descriptions and discussion regarding each individual step will follow. Initially, the placenta tissue is collected from a consenting patient following an elective Cesarean surgery (step 110). The material is preserved and transported in conventional tissue preservation manner to a suitable processing location or facility for check-in and evaluation (step 120). Gross processing, handling, and separation of the amnion and chorion then takes place (step 130). Acceptable tissue is then decontaminated (step 140) and dehydrated (step 145). After decontamination and dehydration, the placental tissue components (e.g., amnion, Wharton's jelly and/or chorion individually or as grafts) are then micronized (step 150). Following micronization, the micronized placental tissue components are incorporated into the aqueous collagen (step 160). Each step is described in detail below.

Initial Tissue Collection (Step 110)

The components used to produce the micronized placental tissue are derived from the placenta. The source of the placenta can vary. In one aspect, the placenta is derived from a mammal, such as human. Other animals including, but not limited to, cows, pigs, and the like can be used herein. In the case of humans, the recovery of the placenta originates in a hospital, where it is collected during a Cesarean section birth. The donor, referring to the mother who is about to give birth, voluntarily submits to a comprehensive screening process designed to provide the safest tissue possible for transplantation. The screening process preferably tests for antibodies to the human immunodeficiency virus type 1 and type 2 (anti-HIV-1 and anti-HIV-2), antibodies to the hepatitis B virus (anti-HBV), hepatitis B surface antigens (HBsAg), antibodies to the hepatitis C virus (anti-HCV), antibodies to the human T-lymphotropic virus type I and type II (anti-HTLV-I, anti-HTLV-II), CMV, and syphilis, and nucleic acid testing for human immune-deficiency virus type 1 (HIV-1) and for the hepatitis C virus (HCV), using conventional serological tests. The above list of tests is by way of example only, as more, fewer, or different tests may be desired or necessary over time or based upon the intended use of the placental components, as will be appreciated by those skilled in the art.

Based upon a review of the donor's information and screening test results, the donor will either be deemed acceptable or not. In addition, at the time of delivery, cultures are taken to determine the presence of bacteria, for example, *Clostridium* or *Streptococcus*. If the donor's information, screening tests, and the delivery cultures are all satisfactory (i.e., do not indicate any risks or indicate acceptable level of risk), the donor is approved by a medical director and the tissue specimen is designated as initially eligible for further processing and evaluation.

Human placentas that meet the above selection criteria are preferably bagged in a saline solution in a sterile shipment bag and stored in a container of wet ice for shipment to a processing location or laboratory for further processing.

If the placenta is collected prior to the completion of obtaining the results from the screening tests and delivery cultures, such tissue is labeled and kept in quarantine. The placenta is approved for further processing only after the required screening assessments and delivery cultures, which declare the tissue safe for handling and use, are satisfied and final approval is obtained from a medical director.

Material Check-In and Evaluation (Step 120)

Upon arrival at the processing center or laboratory, the shipment is opened and verified that the sterile shipment bag/container is still sealed and in the coolant, that the appropriate donor paperwork is present, and that the donor number on the paperwork matches the number on the sterile shipment bag containing the tissue. The sterile shipment bag containing the tissue is then stored in a refrigerator until ready for further processing.

Gross Tissue Processing (Step 130)

When the tissue is ready to be processed further, the sterile supplies necessary for processing the placental tissue are assembled in a staging area in a controlled (i.e., aseptic) environment and are prepared for introduction into the controlled environment. In one aspect, the placenta is processed at room temperature. If the controlled environment is a manufacturing hood, the sterile supplies are opened and placed into the hood using conventional aseptic techniques. If the controlled environment is a clean room, the sterile supplies are opened and placed on a cart covered by a sterile drape. All the work surfaces are covered by a piece of sterile drape using conventional aseptic technique, and the sterile supplies and the processing equipment are placed onto the sterile drape, again using conventional aseptic technique.

Processing equipment is decontaminated according to conventional and industry-approved decontamination procedures and then introduced into the controlled environment. The equipment is strategically placed within the controlled environment to minimize the chance for the equipment to come in proximity to or be inadvertently contaminated by the tissue specimen.

Next, the placenta is removed from the sterile shipment bag and transferred aseptically to a sterile processing basin within the controlled environment. The sterile basin contains hypertonic saline solution (e.g., 18% NaCl) that is at room or near room temperature. The placenta is gently massaged to help separate blood clots and to allow the placental tissue to reach room temperature, which facilitates the separation of the placental components from each other (e.g., amnion membrane and chorion). After having warmed up to ambient temperature (e.g., after about 10-30 minutes), the placenta is then removed from the sterile processing basin and laid flat on a processing tray with the amnion membrane layer facing down for inspection.

The placenta is examined for discoloration, debris or other contamination, odor, and signs of damage. The size of the tissue is also noted. A determination is made, at this point, as to whether the tissue is acceptable for further processing.

The amnion and chorion are next carefully separated. In one aspect, the materials and equipment used in this procedure include a processing tray, 18% saline solution, sterile 4×4 sponges, and two sterile Nalgene jars. The placenta tissue is then closely examined to find an area (typically a corner) in which the amnion can be separated from the chorion. The amnion appears as a thin, opaque layer on the chorion.

The fibroblast layer is identified by gently contacting each side of the amnion with a piece of sterile gauze or a cotton tipped applicator. The fibroblast layer will stick to the test material. The amnion is placed into processing tray basement membrane layer down. Using a blunt instrument, a cell scraper, or sterile gauze, any residual blood is also removed.

This step must be done with adequate care, again, so as not to tear the amnion. The cleaning of the amnion is complete once the amnion is smooth and opaque-white in appearance.

In certain aspects, the intermediate tissue layer, also referred to as the spongy layer, is substantially removed from the amnion in order to expose the fibroblast layer. The term "substantially removed" with respect to the amount of intermediate tissue layer removed is defined herein as removing greater than 90%, greater than 95%, or greater than 99% of the intermediate tissue layer from the amnion. This can be performed by peeling the intermediate tissue layer from the amnion. Alternatively, the intermediate tissue layer can be removed from the amnion by wiping the intermediate tissue layer with gauze or other suitable wipe. The resulting amnion can be subsequently decontaminated using the process described below. Not wishing to be bound by theory, the removal of the intermediate layer can accelerate the drying of the tissue graft, particularly if multiple amnion membranes are used to produce the graft.

Methods described herein allow for retention or removal of substantially all or some of the cellular components of the amnion layers. Removal of cellular components is a technique referred to in the art as "decellularization." Decellularization generally involves the physical and/or chemical removal of all cells present in the amnion, which includes epithelial cells and fibroblast cells. In certain aspects, the amnion is completely decellularized (e.g., removal of epithelial and fibroblast cells). In other aspects, only the epithelial layer or a portion thereof is removed. In yet other aspects, only the fibroblast layer is removed. Optionally, all cellular components are present.

In certain aspects, either a portion of the epithelial layer present on the amnion or substantially all of the epithelial layer is removed in order to expose some or most of the basement layer of the amnion. The term "substantially removed" with respect to the amount of epithelium removed is defined herein as removing greater than 90%, greater than 95%, or greater than 99% of the epithelial cells from the amnion. The presence or absence of epithelial cells remaining on the amnion layer can be evaluated using techniques known in the art. For example, after removal of the epithelial cell layer, a representative tissue sample from the processing lot is placed onto a standard microscope examination slide. The tissue sample is then stained using Eosin Y Stain and evaluated as described below. The sample is then covered and allowed to stand. Once an adequate amount of time has passed to allow for staining, visual observation is done under magnification.

In one embodiment, the epithelial layer can be removed by techniques known in the art. For example, the epithelial layer can be scraped off of the amnion using a cell scraper. Other techniques include, but are not limited to, freezing the membrane, physical removal using a cell scraper, or exposing the epithelial cells to nonionic detergents, anionic detergents, and nucleases. The amount of epithelial layer removed ranges from 0 percent (i.e., the epithelial layer is retained) up to substantially all of the epithelial layer is removed. Intermediate amounts of epithelial layer removal can be achieved by preparing rows of epithelial layer removal intermixed with rows where the epithelial layer is retained. Alternatively, a portion of the epithelial layer is removed while the remainder is retained.

The de-epithelialized tissue is then evaluated to determine that the basement membrane has not been compromised and remains intact. This step is performed after completion of the processing step and the before the tissue has been dehydrated as described in the next section. For example, a representative sample graft is removed for microscopic analysis. The tissue sample is placed onto a standard slide, stained with Eosin Y and viewed under the microscope. If epithelium is present, it will appear as cobblestone-shaped cells.

Chemical Decontamination (Step 140)

The placental tissue components isolated above can be chemically decontaminated using the techniques described below. In one aspect, the amnion and/or chorion is decontaminated at room temperature. In one aspect, the amnion produced in step 130 can be placed into a sterile Nalgene jar for the next step. In one aspect, the following procedure can be used to clean the amnion. A Nalgene jar is aseptically filled with 18% saline hypertonic solution and sealed (or sealed with a top). The jar is then placed on a rocker platform and agitated for between 30 and 90 minutes, which further cleans the amnion of contaminants. If the rocker platform was not in the critical environment (e.g., the manufacturing hood), the Nalgene jar is returned to the controlled/aseptic environment and opened. Using sterile forceps or by aseptically decanting the contents, the amnion is gently removed from the Nalgene jar containing the 18% hypertonic saline solution and placed into an empty Nalgene jar. This empty Nalgene jar with the amnion is then aseptically filled with a pre-mixed antibiotic solution. In one aspect, the premixed antibiotic solution is composed of a cocktail of antibiotics, such as Streptomycin Sulfate and Gentamicin Sulfate. Other antibiotics, such as Polymixin B Sulfate and Bacitracin, or similar antibiotics now available or available in the future, are also suitable. Additionally, it is preferred that the antibiotic solution be at room temperature when added so that it does not change the temperature of or otherwise damage the amnion. This jar or container containing the amnion and antibiotics is then sealed or closed and placed on a rocker platform and agitated for, preferably, between 60 and 90 minutes. Such rocking or agitation of the amnion within the antibiotic solution further cleans the tissue of contaminants and bacteria. Optionally, the amnion can be washed with a detergent. In one aspect, the amnion can be washed with 0.1 to 10%, 0.1 to 5%, 0.1 to 1%, or 0.5% Triton-X wash solution.

If the rocker platform was not in the critical environment (e.g., the manufacturing hood), the jar or container containing the amnion and antibiotics is then returned to the critical/aseptic environment and opened. Using sterile forceps, the amnion is gently removed from the jar or container and placed in a sterile basin containing sterile water or normal saline (0.9% saline solution). The amnion is allowed to soak in place in the sterile water/normal saline solution for at least 10 to 15 minutes. The amnion may be slightly agitated to facilitate removal of the antibiotic solution and any other contaminants from the tissue. After at least 10 to 15 minutes, the amnion is ready to be dehydrated and processed further.

In the case of chorion, the following exemplary procedure can be used. After separation of the chorion from the amnion and removal of clotted blood from the fibrous layer, the chorion is rinsed in 18% saline solution for 15 minutes to 60 minutes. During the first rinse cycle, 18% saline is heated in a sterile container using a laboratory heating plate such that the solution temperature is approximately 48° C. The solution is decanted, the chorion tissue is placed into the sterile container, and decanted saline solution is poured into the container. The container is sealed and placed on a rocker plate and agitated for 15 minutes to 60 minutes. After 1 hour agitation bath, the chorion tissue is removed and placed into second heated agitation bath for an additional 15 minutes to 60 minutes rinse cycle. Optionally, the chorion tissue can be washed with a detergent (e.g., Triton-X wash solution) as discussed above for the decontamination of amnion. The container is sealed and agitated without heat for 15 minutes to 120 minutes. The chorion tissue is next washed with deionized water (250 ml of DI water×4) with vigorous motion for each rinse. The tissue is removed and placed into a container of 1×PBS w/EDTA solution. The container is sealed and agitated for 1 hour at controlled temperature for 8 hours. The chorion tissue is removed and rinsed using sterile water. A visual inspection was performed to remove any remaining discolored fibrous blood material from the chorion tissue. The chorion tissue should have a cream white visual appearance with no evidence of brownish discoloration.

Dehydration (145)

In one aspect, the amnion, chorion, Wharton's jelly, or any combination thereof can be processed into tissue grafts (i.e., laminates) that are subsequently micronized. In another aspect, the individual amnion, chorion, Wharton's jelly layers can be dehydrated independently and subsequently micronized alone or as a mixture of components. In one aspect, the tissue (i.e., individual membrane or graft) is dehydrated by chemical dehydration followed by freeze-drying. In one aspect, the chemical dehydration step is performed by contacting the amnion, chorion, and/or Wharton's jelly with a polar organic solvent for a sufficient time and amount in order to substantially (i.e., greater than 90%, greater than 95%, or greater than 99%) or completely remove residual water present in the tissue (i.e., dehydrate the tissue). The solvent can be protic or aprotic. Examples of polar organic solvents useful herein include, but are not limited to, alcohols, ketones, ethers, aldehydes, or any combination thereof. Specific, non-limiting examples include DMSO, acetone, tetrahydrofuran, ethanol, isopropanol, or any combination thereof. In one aspect, the placental tissue is contacted with a polar organic solvent at room temperature. No additional steps are required, and the tissue can be freeze-dried directly as discussed below.

After chemical dehydration, the tissue is freeze-dried in order to remove any residual water and polar organic solvent. In one aspect, the amnion, chorion, and/or Wharton's jelly can be laid on a suitable drying fixture prior to freeze-drying. For example, one or more strips of amnion can be laid on a suitable drying fixture. Next, chorion is laid on top of the amnion. In this aspect, an amnion/chorion tissue graft is produced. Alternatively, a strip of amnion can be placed on a first drying fixture, and a strip of chorion can be placed on a second drying fixture. The drying fixture is preferably sized to be large enough to receive the placental tissue, fully, in laid out, flat fashion. In one aspect, the drying fixture is made of Teflon or of Delrin, which is the brand name for an acetal resin engineering plastic invented and sold by DuPont and which is also available commercially from Werner Machine, Inc. in Marietta, Georgia Any other suitable material that is heat and cut resistant, capable of being formed into an appropriate shape to receive wet tissue can also be used for the drying fixture.

Once the tissue is placed on the drying fixture, the drying fixture is placed in the freeze-dryer. The use of the freeze-dryer to dehydrate the tissue can be more efficient and thorough compared to other techniques such as thermal dehydration. In general, it is desirable to avoid ice crystal formation in the placental tissue as this may damage the extracellular matrix in the tissue. By chemically dehydrating the placental tissue prior to freeze-drying, this problem can be avoided.

In another aspect, the dehydration step involves applying heat to the tissue. In one aspect, the amnion, chorion, and/or Wharton's jelly is laid on a suitable drying fixture (either as individual strips or as a laminate discussed above), and the drying fixture is placed in a sterile Tyvex (or similar, breathable, heat-resistant, and sealable material) dehydration bag and sealed. The breathable dehydration bag prevents the tissue from drying too quickly. If multiple drying fixtures are being processed simultaneously, each drying fixture is either placed in its own Tyvex bag or, alternatively, placed into a suitable mounting frame that is designed to hold multiple drying frames thereon and the entire frame is then placed into a larger, single sterile Tyvex dehydration bag and sealed.

The Tyvex dehydration bag containing the one or more drying fixtures is then placed into a non-vacuum oven or incubator that has been preheated to approximately 35 to 50 degrees Celcius. The Tyvex bag remains in the oven for between 30 to 120 minutes. In one aspect, the heating step can be performed for 45 minutes at a temperature of approximately 45 degrees Celcius to dry the tissue sufficiently but without over-drying or burning the tissue. The specific temperature and time for any specific oven will need to be calibrated and adjusted based on other factors including altitude, size of the oven, accuracy of the oven temperature, material used for the drying fixture, number of drying fixtures being dried simultaneously, whether a single or multiple frames of drying fixtures are dried simultaneously, and the like.

Preparation of Micronized Compositions (Step 150)

Once the amnion, chorion, and/or Wharton's jelly layer have been dehydrated individually or in the form of a tissue graft, the dehydrated tissue(s) is micronized. The micronized compositions can be produced using instruments known in the art. For example, the Retsch Oscillating Mill MM400 can be used to produce the micronized compositions described herein. The particle size of the materials in the micronized composition can vary as well depending upon the application of the micronized composition. In one aspect, the micronized composition has particles that are less than 500 µm, less than 400 µm, less than 300 µm, or from 25 µm to 300 µm, from 25 µm to 200 µm, or from 25 µm to 150 µm. In certain aspects, particles having a larger diameter (e.g. 150 µm to 350 µm) are desirable. The skill artisan would understand that the particle sizes and size ranges of the materials in the micronized composition of the present invention are the average particle size.

In one aspect, micronization is performed by mechanical grinding or shredding. In another aspect, micronization is performed by cryogenic grinding. In this aspect, the grinding jar containing the tissue is continually cooled with liquid nitrogen from the integrated cooling system before and during the grinding process. Thus the sample is embrittled and volatile components are preserved. Moreover, the denaturing of proteins in the amnion, Wharton's jelly, and/or chorion is minimized or prevented. In one aspect, the CryoMill manufactured by Retsch can be used in this aspect.

The selection of placental tissue components used to make the compositions described herein can vary depending upon the end-use of the composition. For example, placental tissue or individual components such as amnion, chorion, intermediate tissue layer, Wharton's jelly or any combination thereof can be admixed with one another and subsequently micronized. In another aspect, one or more tissue grafts composed of one or more placental tissue, amnion, chorion, Wharton's jelly layers, or any combination thereof (i.e., laminates) can be micronized. In a further aspect, one or more tissue grafts composed of one or more amnion, chorion, Wharton's jelly layer, or any combination thereof can be admixed with amnion, chorion, Wharton's jelly layer, or any combination thereof as individual components and subsequently micronized.

The amount of different components used to make the micronized compositions described herein can vary depending upon the application of the micronized composition. In one aspect, when the micronized composition is composed of amnion (with or without the intermediate tissue layer) and Wharton's jelly, the weight ratio of amnion to Wharton's jelly is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1. In another aspect, when the micronized composition is composed of amnion (with or without the intermediate tissue layer) and chorion, the weight ratio of chorion to amnion is from 10:1 to 1:10, 9:1 to 1:1, 8:1 to 1:1, 7:1 to 1:1, 6:1 to 1:1, 5:1 to 1:1, 4:1 to 1:1, 3:1 to 1:1, 2:1 to 1:1, or about 1:1.

Separation of particle sizes can be achieved, for example, by fractionation of the micronized material in sterile water by forming a suspension of particles. The upper most portion of the suspension will contain predominately the smallest particles and the lower most portion of the suspension will contain predominantly the heaviest particles. Fractionation leads to particle size separation and repeated fractionation will lead to separation of the micronized particles into varying sizes.

The separated particles can be recombined in the desired ratio of particle size as is most appropriate for making the collagen and micronized placental tissue composition and the desired application. As one skilled in the art would appreciate, different sizes of particles result in different flexibility and coherency of the compositions described herein.

In a further aspect, the placental tissues can be cross-linked. For example, a cross-linking agent can be added to the composition (e.g., amnion, chorion, Wharton's jelly, or any combination thereof as individual components and/or as tissue grafts) prior to and/or after micronization. In general, the cross-linking agent is nontoxic and non-immunogenic. When the amnion, Wharton's jelly, and/or chorion (or a tissue graft thereof) are treated with the cross-linking agent, the cross-linking agent can be the same or different. In one aspect, the amnion, Wharton's jelly, and chorion can be treated separately with a cross-linking agent or, in the alternative, the amnion, Wharton's jelly, and chorion can be treated together with the same cross-linking agent. In certain aspects, the amnion, Wharton's jelly, and chorion can be treated with two or more different cross-linking agents. The conditions for treating the amnion, Wharton's jelly, and chorion can vary. In other aspects, the amnion, Wharton's jelly, and/or chorion can be micronized, and the micronized composition can subsequently be treated with a cross-linking agent. In one aspect, the concentration of the cross-linking agent is from 0.1 M to 5 M, 0.1 M to 4 M, 0.1 M to 3 M, 0.1 M to 2 M, or 0.1 M to 1 M.

The cross-linking agent generally possesses two or more functional groups capable of reacting with proteins to produce covalent bonds. In one aspect, the cross-linking agent possesses groups that can react with amino groups present on the protein. Examples of such functional groups include, but are not limited to, hydroxyl groups, substituted or unsubstituted amino groups, carboxyl groups, and aldehyde groups. In one aspect, the cross-linker can be a dialdehyde such as, for example, glutaraldehyde. In another aspect, the cross-linker can be a carbodiimide such as, for example, (N-(3-dimethylaminopropyl)-N'-ethyl-carbodiimide (EDC). In other aspects, the cross-linker can be an oxidized dextran, p-azidobenzoyl hydrazide, N-[alpha-maleimidoacetoxy] succinimide ester, p-azidophenyl glyoxal monohydrate, bis-[beta-(4-azidosalicylamido)ethyl]disulfide, bis-[sulfosuccinimidyl]suberate, dithiobis[succinimidyl]propionate, disuccinimidyl suberate, and 1-ethyl-3-[3-dimethylaminopropyl]carbodiimide hydrochloride, a bifunctional oxirane (OXR), or ethylene glycol diglycidyl ether (EGDE).

In one aspect, sugar is the cross-linking agent, where the sugar can react with proteins present in the amnion, Wharton's jelly, and/or chorion to form a covalent bond. For example, the sugar can react with proteins by the Maillard reaction, which is initiated by the nonenzymatic glycosylation of amino groups on proteins by reducing sugars and leads to the subsequent formation of covalent bonds. Examples of sugars useful as a cross-linking agent include, but are not limited to, D-ribose, glycerose, altrose, talose, ertheose, glucose, lyxose, mannose, xylose, gulose, arabinose, idose, allose, galactose, maltose, lactose, sucrose, cellibiose, gentibiose, melibiose, turanose, trehalose, isomaltose, or any combination thereof.

In certain aspects, the micronized compositions described herein can be formulated in any excipient the biological system or entity can tolerate to produce pharmaceutical compositions. Examples of such excipients include, but are not limited to, water, aqueous hyaluronic acid, saline, Ringer's solution, dextrose solution, Hank's solution, and other aqueous physiologically balanced salt solutions. Nonaqueous vehicles, such as fixed oils, vegetable oils such as olive oil and sesame oil, triglycerides, propylene glycol, polyethylene glycol, and injectable organic esters such as ethyl oleate can also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability. Examples of buffers include phosphate buffer, bicarbonate buffer and Tris buffer, while examples of preservatives include thimerosol, cresols, formalin and benzyl alcohol. In certain aspects, the pH can be modified depending upon the mode of administration. Additionally, the pharmaceutical compositions can include carriers, thickeners, diluents, preservatives, surface active agents and the like in addition to the compounds described herein.

Preparation of Collagen and Micronized Placental Tissue Compositions (Step 160)

Once the placental tissue has been micronized, the micronized placental tissue components are ready to be incorporated into the aqueous/gelatinous collagen. In one aspect the collagen is human, in preferred embodiments the collagen is human placental collagen.

Preferably, the aqueous/gelatinous collagen is soluble (solubilized) collagen. Soluble collagen is markedly different from naturally-occurring collagen which is present in a highly-ordered fibrils. Collagen molecules assemble to form collagen microfibrils and fibrils. Those then undergo natural processing of cross-linking. These are insoluble, crystalline structures. In contrast, the collagen in aqueous solution is present as individual collagen molecules, or can be assembled into collagen fibrils, but will not be cross-linked and can be resolubilized unless cross-linked (i.e., solubility is reversible until the collagen is cross-linked).

The compositions can be prepared using techniques known in the art. As used herein, the term "incorporate" or "incorporated" means to take in, include, absorb, admix, or the like. For example, in one aspect, the composition is prepared by admixing the micronized placental tissue components described herein with a collagen. The term "admixing" is defined as mixing two or more components together (e.g., collagen and micronized placental tissue components) so that there is no chemical reaction or physical interaction. The term "admixing" also includes the chemical reaction or physical interaction between the two or more compounds (e.g., collagen and micronized placental tissue components).

It will be appreciated that the actual preferred amounts of micronized placental tissue components in a specified instance will vary according to the specific utility of the composition, the particular compositions formulated, the mode of application, and the particular situs and subject being treated. Dosages for a given subject can be determined using conventional considerations, e.g. by customary comparison of the differential activities of the subject compounds and of a known agent, e.g., by means of an appropriate conventional pharmacological protocol. Physicians and formulators, skilled in the art of determining doses of pharmaceutical compounds, will have no problems determining dose according to standard recommendations (Physician's Desk Reference, Barnhart Publishing (1999)). In general, the amount of micronized placental tissue components used is an amount sufficient to alter the gelatinous aqueous collagen into a flexible, coherent composition. Without being bound by theory, it is believed that the micronized placental tissue components soak up the water of the hydrated collagen to its maximum resulting in the conversion from a gelatinous composition to a flexible, coherent composition.

The amount of micronized placental components and collagen used to make the compositions described herein can vary depending upon the application. In one aspect, the weight ratio of micronized placental tissue components to collagen is about 300:1 to about 1:1. In one aspect, the weight ratio of micronized placental tissue components to collagen is about 100:1 to about 300:1. Such ratios provide for a coherent mass. Moreover, the flexibility of that mass is inversely proportional to the amount of micronized placental tissue components used. Wherein the greater the amount of micronized placental tissue components, the less flexible the mass. This allows the skilled artisan to select the degree of flexibility for the intended use.

In some embodiments, the weight ratio of micronized placental tissue components to collagen is about 300:1 to about 50:1, about 300:1 to about 75:1, about 300:1 to about 100:1, about 300:1 to about 150:1, about 300:1 to about 200:1, or about 300:1 to about 250:1. In some embodiments, the weight ratio of micronized placental tissue components to collagen is about 100:1 to about 300:1, about 100:1 to about 250:1, about 100:1 to about 200:1, or about 100:1 to about 150:1. Weight ratios may be any values or subranges within any of the recites ranges, including endpoints.

In another aspect the weight ratio of micronized placental tissue components to collagen is from 1:1 to less than 100:1. At these ratios the gelatinous nature of the composition is retained with the understanding that the composition is now augmented by growth factors and cytokines contained within the micronized placental tissue components. In some embodiments, the weight ratio of micronized placental tissue components to collagen is about 1:1 to about 100:1, about 1:1 to about 90:1, about 1:1 to about 80:1, about 1:1 to about 70:1, about 1:1 to about 60:1, about 1:1 to about 50:1, about 1:1 to about 40:1, about 1:1 to about 30:1, about 1:1 to about 20:1, or about 1:1 to about 10:1. In some embodiments, the weight ratio of micronized placental tissue components to collagen is about 10:1 to about 100:1, about 20:1 to about 100:1, about 30:1 to about 100:1, about 40:1 to about 100:1, about 50:1 to about 100:1, about 60:1 to about 100:1, about 70:1 to about 100:1, about 80:1 to about 100:1, or about 90:1 to about 100:1. Weight ratios may be any values or subranges within any of the recites ranges, including endpoints.

One of skill in the art would recognize that the amount of collagen in the composition ranges up to the maximum amount that will form the coherent, flexible composition. In some aspects, the aqueous collagen comprises from about 0.1% to about 2% collagen. In preferred embodiments, the aqueous collagen comprises about 0.5% collagen. In some aspects, the aqueous collagen comprises from about 0.1% to about 1.8% collagen, from about 0.1% to about 1.6% collagen, from about 0.1% to about 1.5% collagen, from about 0.1% to about 1.4% collagen, from about 0.1% to about 1.2% collagen, from about 0.1% to about 1.0% collagen, from about 0.1% to about 0.8% collagen, from about 0.1% to about 0.6% collagen, from about 0.1% to about 0.5% collagen, from about 0.1% to about 0.4% collagen, or from about 0.1% to about 0.2% collagen. In some aspects, the aqueous collagen comprises from about 0.5% to about 2% collagen, from about 0.8% to about 2% collagen, from about 1% to about 2% collagen, from about 1.2% to about 2% collagen, from about 1.5% to about 2% collagen, or from about 1.8% to about 2% collagen. The amount of collagen may be any value or subranges within any of the recites ranges, including endpoints.

In certain embodiments, a composition comprising collagen and micronized placental tissue components has increased flexibility and coherence when sufficient force and shear is applied (e.g., by a syringe) as compared to an aqueous/gelatinous solution of collagen in the absence of micronized placental tissue components. It is to be understood that any type of force and/or shear that causes a change in composition from a gelatinous to a coherent, flexible composition would be embodied by this invention. In preferred embodiments, the force and shear is achieved by ejection through a needle tip. Alternatively, a press or a mold can likewise be used. It is surprising and unexpected that the addition of micronized placental tissue components to collagen resulted in a composition exiting a 27 gauge needle tip that was cohesive and stuck to the needle when raised after injection (See FIG. 3B). That is, the modified placental tissue alters the ejected mass such that it formed a more flexible and/or more coherent structure.

In certain embodiments, the composition is coherent and flexible under physiological conditions, for example, at a temperature range of about 15° C. to about 45° C. In certain embodiments, the composition can be a gel at about 37° C. (e.g., when injected into a subject). Without being bound by theory, it is believed that the collagen and micronized placental tissue component composition would stay at the injection site for a longer period of time as compared to injectable compositions of micronized placental tissue components (e.g., AmnioFix® or EpiFix®) without collagen. Furthermore, without being bound by theory, it is believed that the collagen and micronized placental tissue component composition would break down more slowly as compared to collagen-only compositions. The collagen and micronized placental tissue component composition also is expected to have more growth factors and other factors that aid in healing.

In certain aspects additional components may be added to the collagen and micronized placental tissue component compositions. The additional components may be fillers, bioactive agents, adhesives, stabilizers, buffers, pharmaceutical components, coloring agent, a disintegrating agent, or the like. Additional components may be added to the collagen and/or micronized placental tissue components prior to or after admixing the collagen and micronized placental tissue components.

In one aspect, a filler can be added. Examples of fillers include, but are not limited to, allograft pericardium, allograft acellular dermis, Wharton's jelly separated from vascular structures (i.e., umbilical vein and artery) and surrounding membrane, purified xenograft Type-I collagen, biocellulose polymers or copolymers, biocompatible synthetic polymer or copolymer films, purified small intestinal submucosa, bladder acellular matrix, cadaveric fascia, or any combination thereof.

In another aspect, a bioactive agent can be added to the composition prior to and/or after micronization. Examples of bioactive agents include, but are not limited to, naturally occurring growth factors sourced from platelet concentrates, either using autologous blood collection and separation products, or platelet concentrates sourced from expired banked blood; bone marrow aspirate; stem cells derived from concentrated human placental cord blood stem cells, concentrated amniotic fluid stem cells or stem cells grown in a bioreactor; or antibiotics. Upon application of the composition with bioactive agent to the region of interest, the bioactive agent is delivered to the region over time. Thus, the micronized particles described herein are useful as delivery devices of bioactive agents and other pharmaceutical agents when administered to a subject. Release profiles can be modified based on, among other things, the selection of the components used to make the micronized compositions as well as the size of the particles.

In other aspects, one or more adhesives can be admixed with the collagen and micronized placental compositions. Examples of such adhesives include, but are not limited to, fibrin sealants, cyanoacrylates, gelatin and thrombin products, polyethylene glycol polymer, albumin, and glutaraldehyde products. Not wishing to be bound by theory, a composition composed of smaller micronized particles will produce a denser composition capable of bearing mechanical loads. Alternatively, larger micronized particles will produce constructs that are less dense and possess compressive properties. This feature can be useful in non-load void filling, especially where it is desirable to have a composition that will conform to irregular shapes. The three-dimensional constructs can include one or more bioactive agents described herein.

In one aspect, a coloring agent is added to facilitate in locating and properly placing the collagen and micronized placental tissue component composition to the intended treatment site. In another aspect, a disintegrating agent modifies the rate that the collagen and micronized placental tissue component composition erodes or disintegrates in vivo after being introduced to a subject.

In yet another aspect, the collagen and micronized placental tissue component composition is admixed with at least one plasticizer. One skilled in the art would select a suitable plasticizer based on the biocompatibility of the plasticizer, effect of plasticizer on the degradation or erosion rate of the placental tissue graft in vivo, effect of the plasticizer on the properties of the mixture to facilitate the flexibility and coherency of the collagen and micronized placental tissue component composition. Exemplary plasticizers include, but are not limited to, polyethylene glycol, glucose monoesters and partial fatty acid esters, and the like.

The collagen and micronized placental tissue component compositions described herein can be administered in numerous ways depending on whether local or systemic treatment is desired, and on the area to be treated. In one aspect, administration can be by injection. In other aspects, the composition can be formulated to be applied internally to a subject. In other aspects, the composition can be applied topically (including ophthalmically, vaginally, rectally, intranasally, orally, or directly to the skin).

Optional Preparation of Topical Compositions

In one aspect, the compositions can be formulated as a topical composition applied directly to the skin. Formulations for topical administration can include, emulsions, creams, aqueous solutions, oils, ointments, putty, pastes, gels, lotions, milks and suspensions. In one aspect, the topical composition can include one or more surfactants and/or emulsifiers.

Surfactants (or surface-active substances) that may be present are anionic, non-ionic, cationic and/or amphoteric surfactants. Typical examples of anionic surfactants include, but are not limited to, soaps, alkylbenzenesulfonates, alkanesulfonates, olefin sulfonates, alkyl ether sulfonates, glycerol ether sulfonates, alpha-methyl ester sulfonates, sulfo fatty acids, alkyl sulphates, fatty alcohol ether sulphates, glycerol ether sulphates, fatty acid ether sulphates, hydroxy mixed ether sulphates, monoglyceride (ether) sulphates, fatty acid amide (ether) sulphates, mono- and dialkyl sulfosuccinates, mono- and dialkyl sulfosuccinamates, sulfotriglycerides, amide soaps, ether carboxylic acids and salts thereof, fatty acid isethionates, fatty acid sarcosinates, fatty acid taurides, N-acylamino acids, e.g. acyl lactylates, acyl tartrates, acyl glutamates and acyl aspartates, alkyl oligoglucoside sulphates, protein fatty acid condensates (in particular wheat-based vegetable products) and alkyl (ether) phosphates. Examples of non-ionic surfactants include, but are not limited to, fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides or glucoronic acid derivatives, fatty acid N-alkylglucamides, protein hydrolysates (in particular wheat-based vegetable products), polyol fatty acid esters, sugar esters, sorbitan esters, polysorbates and amine oxides. Examples of amphoteric or zwitterionic surfactants include, but are not limited to, alkylbetaines, alkylamidobetaines, aminopropionates, aminoglycinates, imidazolinium-betaines and sulfobetaines.

In one aspect, the surfactant can be fatty alcohol polyglycol ether sulphates, monoglyceride sulphates, mono- and/or dialkyl sulfosuccinates, fatty acid isethionates, fatty acid sarcosinates, fatty acid taurides, fatty acid glutamates, alpha-olefinsulfonates, ether carboxylic acids, alkyl oligoglucosides, fatty acid glucamides, alkylamidobetaines, amphoacetals and/or protein fatty acid condensates.

Examples of zwitterionic surfactants include betaines, such as N-alkyl-N,N-dimethylammonium glycinates, for example cocoalkyldimethylammonium glycinate, N-acylaminopropyl-N,N-dimethylammonium glycinates, for example cocoacylaminopropyldimethylammonium glycinate, and 2-alkyl-3-carboxymethyl-3-hydroxyethylimidazolines having in each case 8 to 18 carbon atoms in the alkyl or acyl group, and cocoacylaminoethylhydroxyethyl-carboxymethyl glycinate.

In one aspect, the emulsifier can be a nonionogenic surfactant selected from the following: addition products of from 2 to 30 mol of ethylene oxide and/or 0 to 5 mol of propylene oxide onto linear fatty alcohols having 8 to 22 carbon atoms, onto fatty acids having 12 to 22 carbon atoms, onto alkylphenols having 8 to 15 carbon atoms in the alkyl group, and onto alkylamines having 8 to 22 carbon atoms in the alkyl radical; alkyl and/or alkenyl oligoglycosides having 8 to 22 carbon atoms in the alk(en)yl radical and the ethoxylated analogs thereof; addition products of from 1 to 15 mol of ethylene oxide onto castor oil and/or hydrogenated castor oil; addition products of from 15 to 60 mol of ethylene oxide onto castor oil and/or hydrogenated castor oil; partial esters of glycerol and/or sorbitan with unsaturated, linear or saturated, branched fatty acids having 12 to 22 carbon atoms and/or hydroxycarboxylic acids having 3 to 18 carbon atoms, and the adducts thereof with 1 to 30 mol of ethylene oxide; partial esters of polyglycerol (average degree of self-condensation 2 to 8), trimethylolpropane, pentaerythritol, sugar alcohols (e.g. sorbitol), alkyl glucosides (e.g. methyl glucoside, butyl glucoside, lauryl glucoside), and polyglucosides (e.g. cellulose) with saturated and/or unsaturated, linear or branched fatty acids having 12 to 22 carbon atoms and/or hydroxycarboxylic acids having 3 to 18 carbon atoms, and the adducts thereof with 1 to 30 mol of ethylene oxide; mixed esters of pentaerythritol, fatty acids, citric acid and fatty alcohols and/or mixed esters of fatty acids having 6 to 22 carbon atoms, methylglucose and polyols, preferably glycerol or polyglycerol, mono-, di- and trialkyl phosphates, and mono-, di- and/or tri-PEG alkyl phosphates and salts thereof; wool wax alcohols; polysiloxane-polyalkyl-polyether copolymers and corresponding derivatives; and block copolymers, e.g. polyethylene glycol-30 dipolyhydroxystearates. In one aspect, the emulsifier is a polyalkylene glycol such as, for example, polyethylene glycol or polypropylene glycol. In another aspect, the emulsifier is polyethylene glycol having a molecular weight 100 Da to 5,000 Da, 200 Da to 2,500 Da, 300 Da to 1,000 Da, 400 Da to 750 Da, 550 Da to 650 Da, or about 600 Da.

In another aspect, the emulsifier is a poloxamer. In one aspect, the poloxamer is a nonionic triblock copolymer composed of a central hydrophobic chain of polyoxypropylene (e.g., (poly(propylene oxide)) flanked by two hydrophilic chains of polyoxyethylene (e.g., poly(ethylene oxide)). In one aspect, poloxamer has the formula

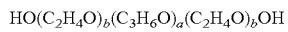

HO(C$_2$H$_4$O)$_b$(C$_3$H$_6$O)$_a$(C$_2$H$_4$O)$_b$OH wherein a is from 10 to 100, 20 to 80, 25 to 70, or 25 to 70, or from 50 to 70; b is from 5 to 250, 10 to 225, 20 to 200, 50 to 200, 100 to 200, or 150 to 200. In another aspect, the poloxamer has a molecular weight from 2,000 to 15,000, 3,000 to 14,000, or 4,000 to 12,000. Poloxamers useful herein are sold under the tradename Pluronic® manufactured by BASF. Non-limiting examples of poloxamers useful herein include, but are not limited to, Pluronic® F68, P103, P105, P123, F127, and L121.

In another aspect, the emulsifier is composed of one or more fatty alcohols. In one aspect, the fatty alcohol is a liner or branched C$_6$ to C$_{35}$ fatty alcohol. Examples of fatty alcohols include, but are not limited to, capryl alcohol (1-octanol), 2-ethyl hexanol, pelargonic alcohol (1-nonanol), capric alcohol (1-decanol, decyl alcohol), undecyl alcohol (1-undecanol, undecanol, hendecanol), lauryl alcohol (dodecanol, 1-dodecanol), tridecyl alcohol (1-tridecanol, tridecanol, isotridecanol), myristyl alcohol (1-tetradecanol), pentadecyl alcohol (1-pentadecanol, pentadecanol), cetyl alcohol (1-hexadecanol), palmitoleyl alcohol (cis-9-hexadecen-1-ol), heptadecyl alcohol (1-n-heptadecanol, heptadecanol), stearyl alcohol (1-octadecanol), isostearyl alcohol (16-methylheptadecan-1-ol), elaidyl alcohol (9E-octadecen-1-ol), oleyl alcohol (cis-9-octadecen-1-ol), linoleyl alcohol (9Z, 12Z-octadecadien-1-ol), elaidolinoleyl alcohol (9E, 12E-octadecadien-1-ol), linolenyl alcohol (9Z, 12Z, 15Z-octadecatrien-1-ol) elaidolinolenyl alcohol (9E, 12E, 15-E-octadecatrien-1-ol), ricinoleyl alcohol (12-hydroxy-9-octadecen-1-ol), nonadecyl alcohol (1-nonadecanol), arachidyl alcohol (1-eicosanol), heneicosyl alcohol (1-heneicosanol), behenyl alcohol (1-docosanol), erucyl alcohol (cis-13-docosen-1-ol), lignoceryl alcohol (1-tetracosanol), ceryl alcohol (1-hexacosanol), montanyl alcohol, cluytyl alcohol (1-octacosanol), myricyl alcohol, melissyl alcohol (1-triacontanol), geddyl alcohol (1-tetratriacontanol), or cetearyl alcohol.

In one aspect, the carrier used to produce the topical composition is a mixture polyethylene and one or more fatty alcohols. For example, the carrier is composed of 50% to 99% by weight, 75% to 99% by weight, 90% to 99% by weight, or about 95% by weight polyethylene glycol and 1% to 50% by weight, 1% to 25% by weight, 1% to 10% by weight, or about 5% by weight fatty alcohol. In a further aspect, the carrier is a mixture of polyethylene glycol and cetyl alcohol.

The topical compositions can also include additional components typically present in such compositions. In one aspect, the topical composition can include one or more of the following components: fats, waxes, pearlescent waxes, bodying agents, thickeners, superfatting agents, stabilizers, polymers, silicone compounds, lecithins, phospholipids, biogenic active ingredients, deodorants, antimicrobial agents, antiperspirants, swelling agents, insect repellents, hydrotropes, solubilizers, preservatives, perfume oils and dyes. Examples of each of these components are disclosed in U.S. Pat. No. 8,067,044, which is incorporated by reference with respect these components.

The topical compositions composed of the collagen and micronized placental tissue component compositions described herein can be prepared by mixing compositions with the carrier. In the case when the carrier is composed of two or more components, the components can be admixed with one another prior to the addition of the collagen and micronized placental tissue component compositions. The amount of collagen and micronized placental tissue component composition present in the topical composition can vary depending upon the application. In one aspect, the collagen and micronized placental tissue component composition is from 0.5% to 20%, 1% to 10%, 2% to 5%, or about 3% by weight of the topical composition.

After preparation, the collagen and micronized placental tissue component compositions can be immediately used or properly packaged for storage and later use.

Optional Preparation of Three-Dimensional Constructs

In one aspect, after the collagen and micronized placental tissue component composition has been prepared, a molded, three-dimensional construct may be produced by applying the collagen and micronized placental tissue component composition to a mold having specific dimensions.

In one aspect, the collagen and micronized placental tissue components are treated with a cross-linking agent described above then placed in a mold having specific dimensions. Alternatively, the collagen and micronized placental tissue component composition is placed into the mold and subsequently treated with the cross-linking agent. In one aspect, the collagen and micronized placental tissue component composition is molded without cross-linking. In one aspect, the collagen and micronized placental tissue component composition is manually formed into any desired shape.

Optional Preparation of Tissue Allografts

In one aspect, after the collagen and micronized placental tissue component composition has been prepared, a coated device may be produced by applying the collagen and micronized placental tissue component composition to one or more sides of a biocompatible material and/or device.

In one aspect, the biocompatible material is a biocompatible mesh that can be made from non-resorbable materials including but not limited to biocompatible metals such as titanium alloys, stainless steel, cobalt-chromium alloys, and nickel-titanium alloys. In another aspect, the layer of biocompatible mesh can be made from non-resorbable polymeric materials, including but not limited to, thermoplastic resins, polyethylenes, ultra-high weight molecular weight polyethylene, high molecular weight polyolefins, uncoated monofilament polypropylene, polyether ether ketone, polyethylene terephthalate, polytetrafluoroethylene, expanded polytetrafluoroethylene, nylon, any polymer or aliphatic hydrocarbons containing one or more double bonds, any other appropriate porous materials, or any other appropriate porous material that can be bent or otherwise formed into a shape.

In another aspect, the biocompatible mesh can be composed of a synthetic or biological resorbable polymeric material including but not limited to polyglycolic acid, poly-L-lactic acid (PLLA), poly-D,L-lactic acid (PDLA), trimethylenecarbonate (TMC), poly-ε-caprolactone, poly-P-dioxanone, copolymers of lactide and glycolide (PLGA), polyhydroxy-3-butyrate, collagen, hyaluronic acid, silk, biocellulose, other protein-based polymers, polysaccharides, poly(DTE carbonate), polyarylates, blends of PLLA, PLDA, or PLGA with TMC and other combinations of these polymers.

In one aspect, the biocompatible mesh is coated on one or both sides with a placental tissue graft and/or the collagen and micronized placental tissue component composition to form a reinforced tissue graft. Examples of reinforced placental tissue allografts and methods of making can be found in U.S. Patent Application Publication No. 2014/0067058, which is incorporated herein by reference in its entirety.

In some aspects, this disclosure relates to tissue grafts comprising one or more layers of placental tissue in combination with one or more layers of a collagen and micronized placental tissue component composition. In one embodiment, the placental tissue graft comprising the collagen and micronized placental tissue composition is a placental tissue graft comprising one or more layers of amnion, one or more layers of chorion, or one or more layers of amnion and chorion. Examples of tissue grafts that can be modified to include a collagen and micronized placental tissue composition as described herein can be found in U.S. Pat. Nos. 8,623,421, 8,709,494, 8,357,403, 8,409,626, and 9,186,382, and U.S. Patent App. Pub. Nos. 2014/0205646, 2014/0343688, and 2013/020676, each of which is incorporated herein by reference in its entirety.

Applications of Collagen and Micronized Placental Tissue Compositions

The collagen and micronized placental tissue component compositions as described herein can be used in numerous medical applications involving wound healing, repairing damaged tendons and cosmetic applications in a subject. The collagen and micronized placental tissue component compositions as described herein can also be used for covering biocompatible materials and/or devices.

In one aspect, the collagen and micronized placental tissue component composition is used in various medical applications without first applying sufficient force and shear to the composition. In other aspects, sufficient force and shear is applied to the composition so as to transform the composition into a coherent, flexible mass prior to use in various medical applications.

In one aspect, the collagen and micronized placental tissue component compositions described herein are useful in enhancing or improving wound healing. The types of wounds that present themselves to physicians on a daily basis are diverse. Acute wounds are caused by surgical intervention, trauma and burns. Chronic wounds are wounds that are delayed in closing compared to healing in an otherwise healthy individual. Examples of chronic wound types plaguing patients include diabetic foot ulcers, venous leg ulcers, pressure ulcers, arterial ulcers, and surgical wounds that become infected.

The physician's goal when treating traumatic wounds is to heal the wound while allowing the patient to retain natural function in the area of the wound with minimal scaring and infection. If a wound becomes infected, it can lead to a loss of limb or life. Large wounds, including burns, are especially difficult to treat because they expose a large surface area to the environment (and thus infection risk), and are susceptible to potentially painful and debilitating scars. Physicians dealing with chronic wounds are mainly concerned with closing the wound as quickly as possible to minimize the risk of an infection that could lead to loss of limb or life. Chronic wounds are wounds on patients that have comorbidities that complicate or delay the healing cascade. In one aspect, the compositions described herein can function as a tissue regeneration template that delivers essential wound healing factors, extracellular matrix proteins and inflammatory mediators to help reduce inflammation, enhance healing, and reduce scar tissue formation.

The collagen and micronized placental tissue component compositions described herein also act as a wound dressing. The compositions may be placed on top of a skin wound which is otherwise open to the environment, thereby functioning as a barrier. The compositions may be in substantially direct contact with the wound and maintain sufficient surface area such that the majority of the wound is covered. Thus, the compositions can provide bioactive factors, scaffold, etc. as required. "Substantially direct contact" refers to contact with the wound, but may be placed over top of, by way of non-limiting example, exudate, medications, a biocompatible mesh, or any other item or medicament as identified by the clinician to be beneficial for healing the wound.

In one aspect, the collagen and micronized placental tissue component composition can be used to repair damaged tendons. The composition can be placed on a damaged tendon to prevent scar formation on the healing tendon. The composition can also provide a protective enclosed environment for the repair to progress successfully.

In other aspects, the collagen and micronized placental tissue component composition described herein can be used in cosmetic applications, such as, for example, plastic surgery procedures. Scar revision is surgery to improve or reduce the appearance of scars. It also restores function and corrects skin changes (disfigurement) caused by an injury, wound, or previous surgery. Scar tissue forms as skin heals after an injury or surgery. The amount of scarring may be determined by the wound size, depth, and location; the person's age; heredity; and skin characteristics including skin color (pigmentation). Surgery involves excision of the scar and careful closure of the defect. In one aspect, the collagen and micronized placental tissue component compositions described herein can be used as a patch to aid in the healing and prevention of scars; and keloid or cancer revision/removal where careful approximation of soft-tissue edges is not achievable and scar tissue can result. Additionally, the anti-inflammatory properties of the micronized placental tissue components can enhance healing as well.

In another aspect, the collagen and micronized placental tissue component compositions described herein can help prevent or reduce wrinkle formation in a subject. In yet another aspect, the compositions can enhance re-epithelization of the dermal skin layer after laser-resurfacing. Compositions described herein can be used alone or in combination with other skin therapies such as, for example, moisturizers, Vitamin (A) creams, vitamin (e), recombinant hyaluronic acid, or human, animal and/or natural oils (e.g., tea tree oil). Compositions containing micronized placental tissue component microparticles having a particle size of about 20 μm to about 100 μm, or of about 25 μm to about 75 μm can be effective in cosmetic applications, such as, prevention or reduction of wrinkle formation in a subject.

In one embodiment, the composition is injected or applied at or proximal to the site of the cosmetic defect, e.g., wrinkle, fine line, abrasion, scar, etc. Additional cosmetic defects that can be treated using the compositions described herein can be found, for example, in U.S. Patent App. Pub. No. 2015/0086634, which is incorporated herein by reference in its entirety.

Without being bound by theory, it is believed that the compositions of the present invention will remain at the site of injection or site of application longer and degrade slower than compositions of either collagen or micronized placental tissue components alone.

In another aspect, the collagen and micronized placental tissue component compositions described herein can be applied to a biocompatible material and/or device such as, for example, an implantable medical device. Implantable medical devices can be coated with one or more collagen and micronized placental tissue component compositions described herein to provide a device with beneficial properties when used in living tissue (e.g., enhanced wound healing and the prevention of scaring).

Examples of suitable implantable devices that can be coated with the collagen and micronized placental tissue component compositions described herein include, but are not limited to, coronary stents, peripheral stents, implants (e.g., dental, orthopedic, spinal), catheters, arterio-venous grafts, by-pass grafts, pacemaker and defibrillator leads, anastomotic clips, arterial closure devices, patent foramen ovale closure devices, and drug delivery balloons. The implantable device can be made of any suitable biocompatible materials, including biostable and bioabsorbable materials. Suitable biocompatible metallic materials include, but are not limited to, stainless steel, tantalum, titanium alloys (including nitinol), and cobalt alloys (including cobalt-chromium-nickel and cobalt-chromium-tungsten alloys). Suitable nonmetallic biocompatible materials include, but are not limited to, polyamides, fluoropolymers, polyolefins (i.e. polypropylene, polyethylene etc.), nonabsorbable polyesters (i.e. polyethylene terephthalate), and bioabsorbable aliphatic polyesters (i.e. homopolymers and copolymers of lactic acid, glycolic acid, lactide, glycolide, para-dioxanone, trimethylene carbonate, epsilon-caprolactone, and the like, and combinations of these).

In other aspects, the collagen and micronized placental tissue component compositions described herein can be applied to wound healing devices. For example, the wound healing device can be a bandage, wrap, gauze, suture, or any other device used to treat wound. In these aspects, the collagen and micronized placental tissue component composition can be coated on and/or impregnated within the device. In other aspects, the wound healing device can be a membrane or graft used in wound healing applications, where the micronized composition is coated on one or more sides of the membrane or graft. For example, any of the tissue grafts described herein that are a precursor to the micronized compositions can be coated with the compositions.

EXAMPLES

The following examples are put forth so as to provide those of ordinary skill in the art with a complete disclosure and description of how the compositions and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

Example 1

Micronized placental tissue components used here were produced by the process described in US App. Pub. No. 2013/0344162, which is incorporated by reference in its entirety.

Figure 2A:
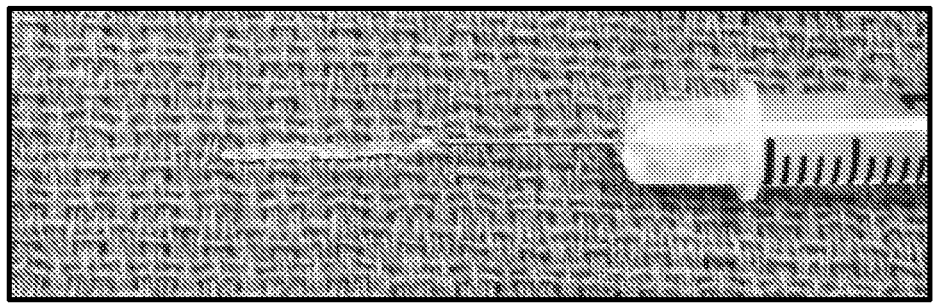
FIGS. 2A and 2B illustrate an aqueous collagen composition (FIG. 2A) and a collagen and micronized placental tissue composition (FIG. 2B) as they are ejected from a 27 gauge needle.
Figure 2B:
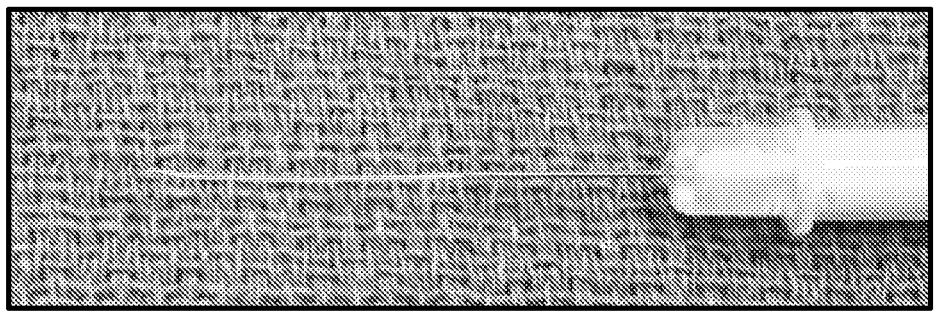
Figure 3A:
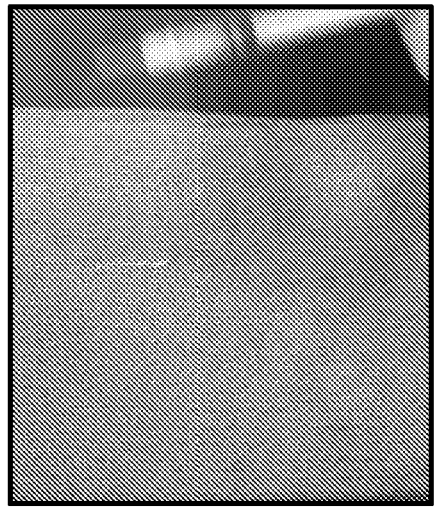
FIGS. 3A and 3B illustrate the lack of tensile strength of a hydrated collagen composition (FIG. 3A) as compared to a composition comprising collagen and micronized placental tissue (FIG. 3B).
Figure 3B:
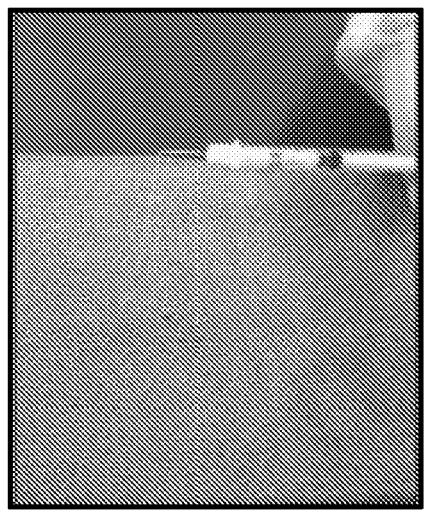
Figure 4:
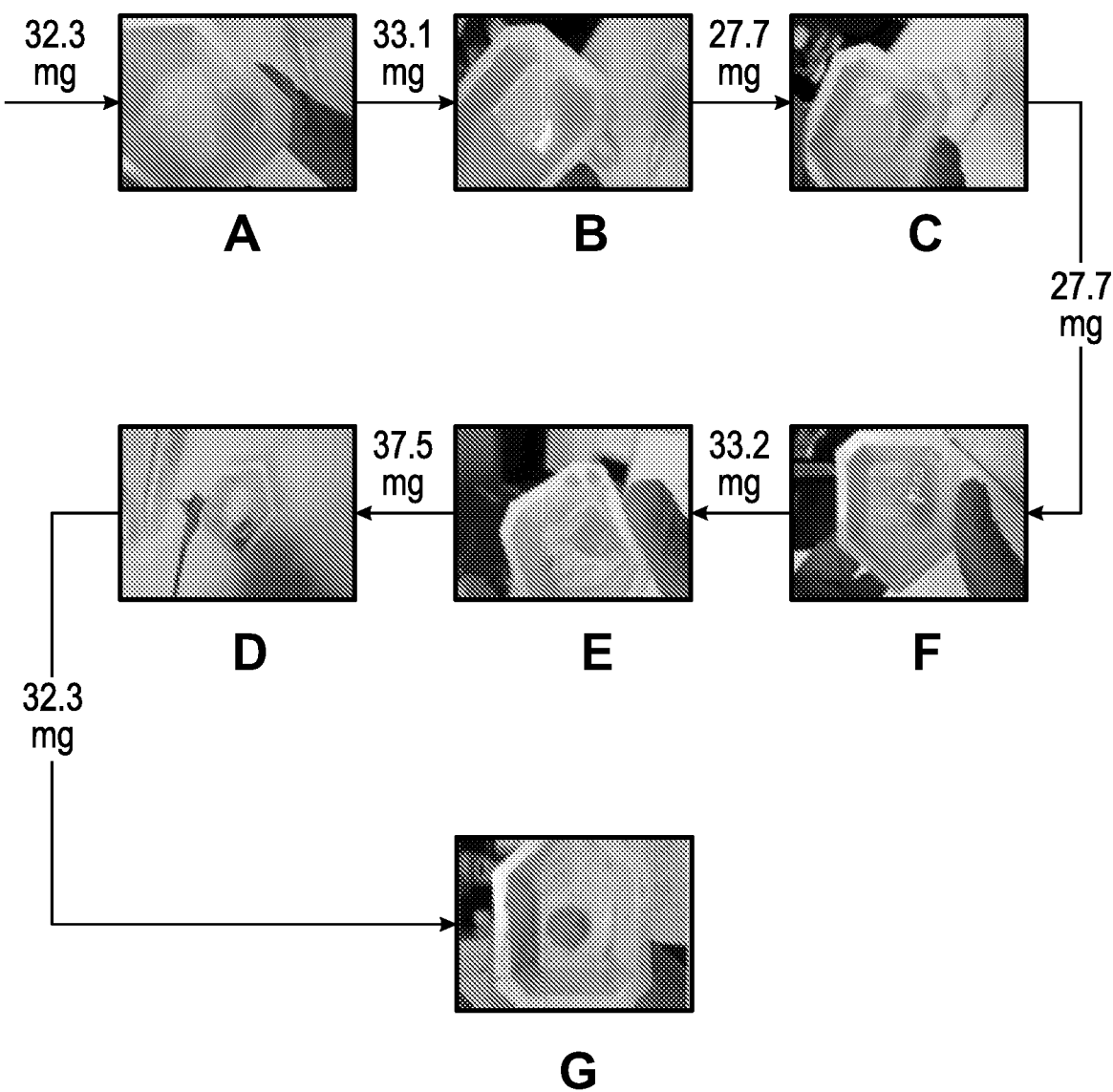
FIG. 4 illustrates the sequential addition of micronized placental tissue components into an aqueous collagen material. At panel A, 32.3 mg of micronized placental tissue components was admixed with 1 mL of 0.469% (4.69 mg) neutralized collagen. At panel B, 33.1 mg of micronized placental tissue components was admixed with the composition from panel A. At panel C, 27.7 mg of micronized placental tissue components was admixed with the composition from panel B. At panel D, 33.9 mg of micronized placental tissue components was admixed with the composition from panel C. At panel E, 33.2 mg of micronized placental tissue components was admixed with the composition from panel D. At panel F, 37.5 mg of micronized placental tissue components was admixed with the composition from panel E. At panel G, 36.3 mg of micronized placental tissue components was admixed with the composition from panel F. The composition in panel G comprises a total of 234 mg micronized placental tissue components and 4.69 mg collagen in 1 mL of an aqueous solution.
Figure 5:
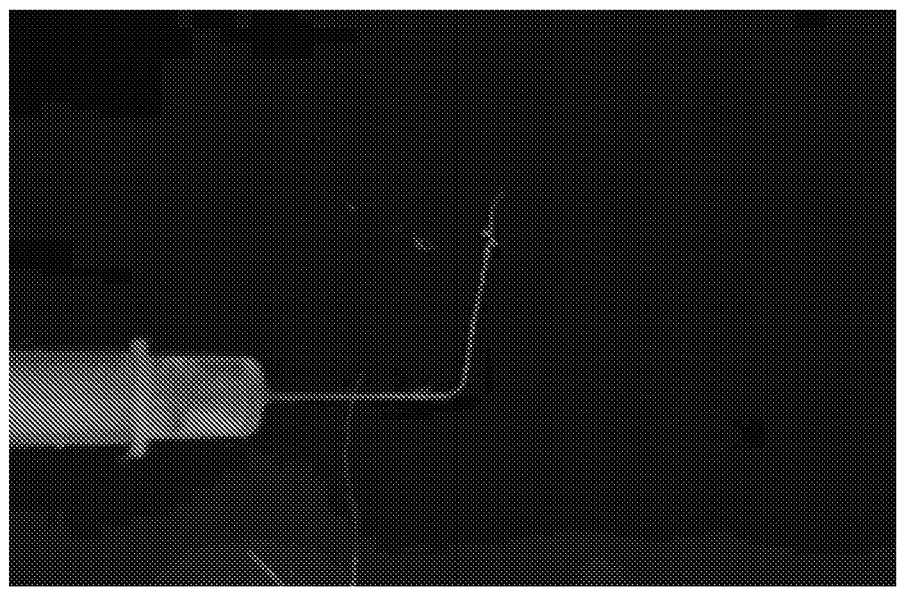
FIG. 5 illustrates applying the composition of panel G in FIG. 4 under sufficient force and shear through a 27-gauge needle so as to transform the composition into a coherent, flexible mass.

A composition of ~5 mg aqueous/gelatinous placental collagen alone, when ejected from a 27 gauge needle, retained the same aqueous/gelatinous characteristics (FIG. 2A). Such composition also had a low tensile strength such that when the needle was raised at a 90 degree angle the composition broke off of the needle tip (FIG. 3A). In contrast, when micronized placental tissue was added to 1 mL of ~0.5% human placental collagen (~5 mg collagen) in sequential additions (up to a total amount of about 230 mg micronized placental tissue; See, FIG. 4) and ejected through a 27 gauge needle there was a composition change whereby gelatinous material changed to a flexible, cohesive composition (FIG. 2B). Surprisingly, this flexible, cohesive composition also had greater tensile strength than the composition of aqueous/gelatinous placental collagen such that when the needle was raised at a 90 degree angle the composition remained attached (FIG. 3B and FIG. 5).

Various modifications and variations can be made to the compounds, compositions and methods described herein. Other aspects of the compounds, compositions and methods described herein will be apparent from consideration of the specification and practice of the compounds, compositions and methods disclosed herein. It is intended that the specification and examples be considered as exemplary.

What is claimed is:

1. A composition comprising water, soluble collagen and micronized placental tissue components such that the composition is an integrated admixture having apparent homogeneity, wherein the composition is an aqueous or gelatinous composition which forms a coherent and flexible mass when force and/or shear is applied.

2. The composition of claim 1, wherein the micronized placental tissue components comprise micronized amnion, micronized chorion, micronized Wharton's jelly, or any combination thereof.

3. The composition of claim 1, wherein the micronized placental tissue components have a particle size less than 400 μm.

4. The composition of claim 1, wherein the micronized placental tissue components comprise a micronized tissue graft comprising an amnion layer and a chorion layer, wherein the chorion layer is layered directly over the amnion layer, and further wherein the amnion layer has an exposed basement membrane and an intact fibroblast component.

5. The composition of claim 1, wherein the micronized placental tissue components comprise a micronized tissue graft comprising an amnion layer and a chorion layer, wherein the chorion layer is layered directly over the amnion layer, and further wherein the amnion layer has an intact epithelial cell layer and an intact fibroblast component.

6. The composition of claim 1, wherein the collagen is human collagen.

7. The composition of claim 1, wherein the collagen is an aqueous collagen material comprising from about 0.1% to about 2% collagen.

8. The composition of claim 1, wherein the weight ratio of the micronized placental tissue components to the collagen is from about 3:1 to about 100:1.

9. The composition of claim 1, wherein the weight ratio of micronized placental tissue components to collagen is about 100:1 to about 300:1.

10. The composition of claim 1, wherein the composition is obtained by ejecting a precursor composition comprising aqueous/gelatinous collagen and micronized placental tissue components.

11. A method for transforming an aqueous/gelatinous collagen mass into a coherent and flexible composition said method comprising:
   a. incorporating sufficient micronized placental tissue components into an aqueous collagen material; and
   b. applying sufficient force and shear to the composition so as to transform the composition into a coherent, flexible mass.

12. The method of claim 11, wherein the aqueous collagen material comprises from about 0.1% to about 2% collagen.

13. The method of claim 11, wherein the micronized placental tissue components comprise micronized amnion, micronized chorion, micronized Wharton's jelly, or any combination thereof.

14. The method of claim 11, wherein the placental tissue components have a particle size less than 400 μm.

15. The method of claim 11, wherein the collagen is human collagen.

16. The method of claim 11, wherein the weight ratio of the micronized placental tissue components to the collagen is from about to about 100:1 to about 300:1.

17. A method for treating a wound in a subject in need thereof comprising administering to the wound an effective amount of the composition of claim 1.

18. A method for treating a cosmetic defect in a subject in need thereof comprising administering to the wound an effective amount of the composition of claim 1.

* * * * *

UNITED STATES PATENT AND TRADEMARK OFFICE
CERTIFICATE OF CORRECTION

| | | |
|---|---|---|
| PATENT NO. | : 12,070,528 B2 | Page 1 of 1 |
| APPLICATION NO. | : 16/989170 | |
| DATED | : August 27, 2024 | |
| INVENTOR(S) | : Thomas J. Koob et al. | |

It is certified that error appears in the above-identified patent and that said Letters Patent is hereby corrected as shown below:

In the Claims

In Column 25, Line 33, Claim 9, delete "about" and insert -- from about --, therefor.
In Column 26, Line 26, Claim 16, delete "about to about" and insert -- about --, therefor.

Signed and Sealed this
Eighteenth Day of February, 2025

Coke Morgan Stewart
*Acting Director of the United States Patent and Trademark Office*